(12) United States Patent
Levy et al.

(10) Patent No.: US 10,144,926 B2
(45) Date of Patent: Dec. 4, 2018

(54) METHOD OF RAPID ISOLATION OF APTAMER BEACONS

(71) Applicant: ALBERT EINSTEIN COLLEGE OF MEDICINE, INC., Bronx, NY (US)

(72) Inventors: Matthew Levy, New Rochelle, NY (US); Simon G. Trevino, Bronx, NY (US)

(73) Assignee: Albert Einstein College of Medicine, Inc., Bronx, NY (US)

( * ) Notice: Subject to any disclaimer, the term of this patent is extended or adjusted under 35 U.S.C. 154(b) by 0 days.

(21) Appl. No.: 15/101,987

(22) PCT Filed: Dec. 12, 2014

(86) PCT No.: PCT/US2014/069981
§ 371 (c)(1),
(2) Date: Jun. 6, 2016

(87) PCT Pub. No.: WO2015/094958
PCT Pub. Date: Jun. 25, 2015

(65) Prior Publication Data
US 2016/0304857 A1    Oct. 20, 2016

Related U.S. Application Data

(60) Provisional application No. 61/917,548, filed on Dec. 18, 2013.

(51) Int. Cl.
*C07H 21/04* (2006.01)
*C12N 15/10* (2006.01)
*C12Q 1/6811* (2018.01)
*C12N 15/115* (2010.01)

(52) U.S. Cl.
CPC ........ *C12N 15/1048* (2013.01); *C12N 15/115* (2013.01); *C12Q 1/6811* (2013.01); *C12N 2310/16* (2013.01)

(58) Field of Classification Search
CPC ................ C12Q 1/68; C12N 15/111
See application file for complete search history.

(56) References Cited

U.S. PATENT DOCUMENTS

| | | |
|---|---|---|
| 2010/0015608 A1 | 1/2010 | Kolpashchikov |
| 2011/0263459 A1 | 10/2011 | Borer et al. |
| 2013/0123478 A1 | 5/2013 | Levy et al. |
| 2014/0363493 A1 | 12/2014 | Palliser et al. |
| 2015/0125516 A1 | 5/2015 | Levy et al. |
| 2015/0191730 A1 | 7/2015 | Levy et al. |
| 2016/0266133 A1 | 9/2016 | Levy |

FOREIGN PATENT DOCUMENTS

| | | |
|---|---|---|
| WO | 20015066001 A1 | 5/2015 |
| WO | 2016057597 A1 | 4/2016 |

OTHER PUBLICATIONS

Shangguan et al. Anal Chem 2008, 721-728.*
PCT Notification Concerning Transmittal of International Preliminary Report on Patentability and Written Opinion of the International Searching Authority, dated Jun. 21, 2016 in connection with PCT International Patent Application No. PCT/US2014/069981, 8 pages.
PCT International Search Report and Written Opinion, dated May 28, 2015 in connection with PCT International Application No. PCT/US2014/069981, 14 pages.

* cited by examiner

*Primary Examiner* — Kimberly Chong
(74) *Attorney, Agent, or Firm* — Amster, Rothstein & Ebenstein LLP

(57) ABSTRACT

Methods and compositions are provided for rapidly identifying novel structure-switching aptamers.

15 Claims, 10 Drawing Sheets
Specification includes a Sequence Listing.

3(a)  3(b)  3(c)  3(d)

SEQUENCE LISTING

```
<160> NUMBER OF SEQ ID NOS: 23

<210> SEQ ID NO 1
<211> LENGTH: 39
<212> TYPE: DNA
<213> ORGANISM: Artificial Sequence
<220> FEATURE:
<223> OTHER INFORMATION: chemically synthesized aptamer
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (20)..(23)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t

<400> SEQUENCE: 1
ctcgggacnn ggattttccn nnnacgaagt nntcccgag                       39

<210> SEQ ID NO 2
<211> LENGTH: 39
<212> TYPE: DNA
<213> ORGANISM: Artificial Sequence
<220> FEATURE:
<223> OTHER INFORMATION: chemically synthesized aptamer

<400> SEQUENCE: 2
ctcgggacgt ggattttcca catacgaagt tgtcccgag                       39

<210> SEQ ID NO 3
<211> LENGTH: 39
<212> TYPE: DNA
<213> ORGANISM: Artificial Sequence
<220> FEATURE:
<223> OTHER INFORMATION: chemically synthesized aptamer

<400> SEQUENCE: 3
ctcgggacgt ggattttccg catacgaagt tgtcccgag                       39

<210> SEQ ID NO 4
<211> LENGTH: 39
<212> TYPE: DNA
<213> ORGANISM: Artificial Sequence
<220> FEATURE:
<223> OTHER INFORMATION: chemically synthesized aptamer

<400> SEQUENCE: 4
ctcgggacat ggattttcca taaacgaagt ggtcccgag                       39

<210> SEQ ID NO 5
<211> LENGTH: 30
<212> TYPE: DNA
<213> ORGANISM: Artificial Sequence
<220> FEATURE:
<223> OTHER INFORMATION: chemically synthesized aptamer

<400> SEQUENCE: 5
gacatggatt ttccataaac gaagtgggtc                                30

<210> SEQ ID NO 6
<211> LENGTH: 43
<212> TYPE: DNA
<213> ORGANISM: Artificial Sequence
```

```
<220> FEATURE:
<223> OTHER INFORMATION: chemcially synthesized aptamer
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (21)..(27)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t

<400> SEQUENCE: 6
ctcgggacnn nggatttttcc nnnnnnnacg aagtnntccc gag            43

<210> SEQ ID NO 7
<211> LENGTH: 43
<212> TYPE: DNA
<213> ORGANISM: Artificial Sequence
<220> FEATURE:
<223> OTHER INFORMATION: chemically synthesized aptamer

<400> SEQUENCE: 7
ctcgggacgt tggatttttcc caaacatacg aagttgtccc gag            43

<210> SEQ ID NO 8
<211> LENGTH: 39
<212> TYPE: DNA
<213> ORGANISM: Artificial Sequence
<220> FEATURE:
<223> OTHER INFORMATION: chemically synthesized aptamer

<400> SEQUENCE: 8
ctcgggacgt ggatttttccg catacgaagt tgtcccgag                39

<210> SEQ ID NO 9
<211> LENGTH: 43
<212> TYPE: DNA
<213> ORGANISM: Artificial Sequence
<220> FEATURE:
<223> OTHER INFORMATION: chemically synthesized aptamer

<400> SEQUENCE: 9
ctcgggacgt tggatttttcc tatactaacg aagtggtccc gag            43

<210> SEQ ID NO 10
<211> LENGTH: 30
<212> TYPE: DNA
<213> ORGANISM: Artificial Sequence
<220> FEATURE:
<223> OTHER INFORMATION: chemically synthesized aptamer

<400> SEQUENCE: 10
gacgtggatt ttccactaac gaagtgggtc                           30

<210> SEQ ID NO 11
<211> LENGTH: 43
<212> TYPE: DNA
<213> ORGANISM: Artificial Sequence
<220> FEATURE:
<223> OTHER INFORMATION: chemically synthesized aptamer

<400> SEQUENCE: 11
ctcgggactc aggatttttcc atccggtacg aagtagtccc gag            43
```

<210> SEQ ID NO 12
<211> LENGTH: 30
<212> TYPE: DNA
<213> ORGANISM: Artificial Sequence
<220> FEATURE:
<223> OTHER INFORMATION: chemically synthesized aptamer

<400> SEQUENCE: 12
gacacggatt ttcctccgac gaagtgagtc                                    30

<210> SEQ ID NO 13
<211> LENGTH: 43
<212> TYPE: DNA
<213> ORGANISM: Artificial Sequence
<220> FEATURE:
<223> OTHER INFORMATION: chemically synthesized aptamer

<400> SEQUENCE: 13
ctcgggacgt aggatttttcc cttcggcacg aagtcgtccc gag                    43

<210> SEQ ID NO 14
<211> LENGTH: 43
<212> TYPE: DNA
<213> ORGANISM: Artificial Sequence
<220> FEATURE:
<223> OTHER INFORMATION: chemically synthesized aptamer

<400> SEQUENCE: 14
ctcgggacgc cggatttttcc cgagcacacg aagttgtccc gag                    43

<210> SEQ ID NO 15
<211> LENGTH: 43
<212> TYPE: DNA
<213> ORGANISM: Artificial Sequence
<220> FEATURE:
<223> OTHER INFORMATION: chemcially synthesized aptamer

<400> SEQUENCE: 15
ctcgggacag tggatttttcc agtccacacg aagttgtccc gag                    43

<210> SEQ ID NO 16
<211> LENGTH: 43
<212> TYPE: DNA
<213> ORGANISM: Artificial Sequence
<220> FEATURE:
<223> OTHER INFORMATION: chemically synthesized aptamer

<400> SEQUENCE: 16
ctcgggacag tggatttttcc tatacacacg aagttgtccc gag                    43

<210> SEQ ID NO 17
<211> LENGTH: 42
<212> TYPE: DNA
<213> ORGANISM: Artificial Sequence
<220> FEATURE:
<223> OTHER INFORMATION: chemically synthesized aptamer

<400> SEQUENCE: 17
ctcgggaccg tggatttttcc gagccacacg aagtggtccc ga                     42

<210> SEQ ID NO 18
<211> LENGTH: 34
<212> TYPE: DNA
<213> ORGANISM: Artificial Sequence
<220> FEATURE:
<223> OTHER INFORMATION: primer

```
<400> SEQUENCE: 18
cctcaatacc accacgtatt catgcgagat ggcc                                34

<210> SEQ ID NO 19
<211> LENGTH: 13
<212> TYPE: DNA
<213> ORGANISM: Artificial Sequence
<220> FEATURE:
<223> OTHER INFORMATION: primer

<400> SEQUENCE: 19
gtcccgagag cag                                                       13

<210> SEQ ID NO 20
<211> LENGTH: 58
<212> TYPE: DNA
<213> ORGANISM: Artificial Sequence
<220> FEATURE:
<223> OTHER INFORMATION: primer

<400> SEQUENCE: 20
ctggtcatgg cgggcattta attcaattac gtggtcatcg tcctggtggc catctcgc      58

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
agtcgtacgt taggaggact                                                20

<210> SEQ ID NO 22
<211> LENGTH: 143
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (95)..(96)
<223> OTHER INFORMATION: n is a, c, g, or t
<220> FEATURE:
<221> NAME/KEY: misc_feature
<222> LOCATION: (106)..(109)
<223> OTHER INFORMATION: n is a, c, g, or t
<220> FEATURE:
<221> NAME/KEY: misc_feature
<222> LOCATION: (117)..(118)
<223> OTHER INFORMATION: n is a, c, g, or t

<400> SEQUENCE: 22
ctggtcatgg cgggcattta attcaattac gtggtcatcg tcctggtggc catctcgcat    60
gaatacgtgg tggtattgag gctgctctcg ggacnnggat tttccnnnna cgaagtnntc   120
ccgagtcctc ctaacgtacg act                                          143

<210> SEQ ID NO 23
<211> LENGTH: 147
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (95)..(97)
```

```
<223> OTHER INFORMATION: n is a, c, g, or t
<220> FEATURE:
<221> NAME/KEY: misc_feature
<222> LOCATION: (107)..(113)
<223> OTHER INFORMATION: n is a, c, g, or t
<220> FEATURE:
<221> NAME/KEY: misc_feature
<222> LOCATION: (121)..(122)
<223> OTHER INFORMATION: n is a, c, g, or t

<400> SEQUENCE: 23
ctggtcatgg cgggcattta attcaattac gtggtcatcg tcctggtggc catctcgcat        60
gaatacgtgg tggtattgag gctgctctcg ggacnnngga ttttccnnnn nnnacgaagt       120
nntcccgagt cctcctaacg tacgact                                           147
```

METHOD OF RAPID ISOLATION OF APTAMER BEACONS

CROSS-REFERENCE TO RELATED APPLICATIONS

This application is a U.S. national stage entry under 35 U.S.C. § 371 of PCT International Patent Application No. PCT/US2014/069981, filed Dec. 12, 2014, which claims priority of U.S. Provisional Application No. 61/917,548, filed Dec. 18, 2013, the contents of each of which are incorporated herein by reference into the subject application.

STATEMENT OF GOVERNMENT SUPPORT

This invention was made with government support under grant numbers NIH R21 CA157366 and NIH R21 CA182330 awarded by the National Institutes of Health, National Cancer Institute. The government has certain rights in the invention.

BACKGROUND OF THE INVENTION

The disclosures of all publications, patents, patent application publications and books referred to in this application are hereby incorporated by reference in their entirety into the subject application to more fully describe the art to which the subject invention pertains.

The detection of biological and chemical agents of consequence for human health is an ongoing goal for various biotechnology platforms (1). Towards this end, nucleic acids that bind to small molecules in a highly specific manner, aptamers, have garnered interest for their ease of synthesis and quality control. A special class of aptamers, structure-switching aptamer beacons, contain intra-duplexes or inter-duplexes that are covalently linked to quencher and fluorescent probes. Upon binding of a target molecule, the proximity of the probes is disrupted, rendering the device fluorescent (2, 3).

These aptamer beacons have been generated via one of two general strategies. In the first approach, known aptamers are rationally modified by the addition of short sequence extensions. These additional bases serve to disrupt the aptamer's native fold and to introduce a fluorophore and quencher pair that can be attached covalently (4-7) (FIG. 1a) or by hybridization (8). In this latter example, both two-piece and three-piece aptamer beacons have been developed (FIG. 1b,c).

Second, structural-switching aptamers have been directly acquired through in vitro selection (9-12). Here, random nucleic acid libraries are typically immobilized on a support via hybridization (FIG. 1d). Following target addition, sequences that selectively bind a given target are released from the matrix if the binding event induces a structural rearrangement wherein an internal complementary sequence of the aptamer is preferentially bound. DNAs that are eluted in this fashion are PCR-amplified to seed a new, enriched library for use in subsequent rounds of selection. Recently, several steroid-binding aptamers were isolated from a DNA library that included a designed three-way junction containing eight variable bases (13)—a surprising result given the library contained less than $10^5$ unique sequences. However, it is noted that even when using a small library such as this, the identification of functional aptamer beacons required 9 to 13 rounds of selection. Additionally, the selected molecules were not in and of themselves fluorescent sensors and had to be adapted and optimized for this purpose, further complicating the process of generating these sensors.

The present invention addresses the need for better methods for selection and identification of structural-switching aptamers or aptamer beacons.

SUMMARY OF THE INVENTION

This invention provides a streamlined approach for isolating structure switching aptamers that have widespread use in target detection.

This invention provides a method of identifying an aptamer for a predetermined target comprising:
contacting the predetermined target with a plurality of candidate oligonucleotide aptamers each attached to a microbead, wherein each candidate oligonucleotide aptamer (i) has hybridized thereto a second oligonucleotide having a fluorophore attached thereto, and (ii) also has hybridized thereto a third oligonucleotide having a quenching moiety attached thereto, wherein the third oligonucleotide having the quenching moiety is displaced from the candidate oligonucleotide aptamer if the candidate oligonucleotide aptamer binds to a target, and
recovering any microbeads that show an increase in fluorescence after contacting with the predetermined target as compared to fluorescence of the plurality before contacting with the predetermined target,
wherein the candidate oligonucleotide aptamer attached to a microbead so recovered is identified as an aptamer for the predetermined target.

This invention also provides an aptamer comprising:

```
                                         (SEQ ID NO: 13)
ctcgggacgtaggatttccccttcggcacgaagtcgtcccgag (SEQ ID NO: 14)
ctcgggacgccggattttcccgagcacacgaagttgtcccgag (SEQ ID NO: 15)
ctcgggacagtggattttccagtccacacgaagttgtcccgag (SEQ ID NO: 16)
ctcgggacagtggattttcctatacacacgaagttgtcccgag (SEQ ID NO: 17)
ctcgggaccgtggattttccgagccacacgaagtggtcccgag
or
                                          (SEQ ID NO: 2)
ctcgggacgtggattttccacatacgaagttgtcccgag.
```

This invention also provides a method of identifying an aptamer for a predetermined target comprising:
contacting the predetermined target with a plurality of candidate oligonucleotide aptamers each attached to a microbead, wherein each candidate oligonucleotide aptamer (i) has hybridized thereto a second oligonucleotide having a first fluorophore of a FRET pair attached thereto, and (ii) also has hybridized thereto a third oligonucleotide having a second fluorophore of the FRET pair attached thereto, wherein the third oligonucleotide having the second fluorophore of the FRET pair is displaced from the candidate oligonucleotide aptamer if the candidate oligonucleotide aptamer binds to a target, and
recovering any microbeads that show a change in fluorescence after contacting with the predetermined target as compared to fluorescence of the plurality before contacting with the predetermined target, wherein the candidate oligonucleotide aptamer attached to a microbead so recovered is identified as an aptamer for the predetermined target.

This invention also provides a method of identifying an aptamer for a predetermined target comprising:

contacting the predetermined target with a plurality of candidate oligonucleotide aptamers each attached to a microbead, wherein each candidate oligonucleotide aptamer (i) has attached thereto a fluorophore, and (ii) also has hybridized thereto another oligonucleotide having a quenching moiety attached thereto, wherein the oligonucleotide having the quenching moiety is displaced from the candidate oligonucleotide aptamer if the candidate oligonucleotide aptamer binds to a target, and recovering any microbeads that show an increase in fluorescence after contacting with the predetermined target as compared to fluorescence of the plurality before contacting with the predetermined target, wherein the candidate oligonucleotide aptamer attached to a microbead so recovered is identified as an aptamer for the predetermined target.

This invention also provides a method of identifying an aptamer for a predetermined target comprising:

contacting the predetermined target with a plurality of candidate oligonucleotide aptamers each attached to a microbead, wherein each candidate oligonucleotide aptamer (i) has hybridized thereto a first fluorophore of a FRET pair attached thereto, and (ii) also has hybridized thereto another oligonucleotide having a second fluorophore of the FRET pair attached thereto, wherein the oligonucleotide having the second fluorophore of the FRET pair is displaced from the candidate oligonucleotide aptamer if the candidate oligonucleotide aptamer binds to a target, and recovering any microbeads that show a change in fluorescence after contacting with the predetermined target as compared to fluorescence of the plurality before contacting with the predetermined target, wherein the candidate oligonucleotide aptamer attached to a microbead so recovered is identified as an aptamer for the predetermined target.

This invention also provides a method of identifying a deoxyribozyme for a predetermined target comprising:

contacting the predetermined target with a plurality of candidate deoxyribozymes each attached to a microbead, wherein each candidate deoxyribozyme (i) has attached thereto a fluorophore, and (ii) also has attached thereto a quenching moiety, wherein in the unbound state of the deoxyribozyme the fluorophore and quenching moiety are sufficiently far apart that the quenching moiety does not quench the fluorophore, and wherein when the deoxyribozyme binds to a target it folds such that the quenching moiety does quench the fluorophore, and recovering any microbeads that show an decrease in fluorescence after contacting with the predetermined target as compared to fluorescence of the plurality before contacting with the predetermined target, wherein the deoxyribozyme attached to a microbead so recovered is identified as an aptamer for the predetermined target.

This invention also provides a method of identifying an deoxyribozyme for a predetermined target comprising:

contacting the predetermined target with a plurality of candidate deoxyribozymes each attached to a microbead, wherein each candidate deoxyribozyme (i) has attached thereto a fluorophore, and (ii) also has attached thereto a quenching moiety, wherein in the unbound state of the candidate deoxyribozyme the fluorophore and quenching moiety are sufficiently close together that the quenching moiety quenches the fluorophore, and wherein when the candidate deoxyribozyme binds to a target it folds such that the quenching moiety does not quench the fluorophore, and recovering any microbeads that show an increase in fluorescence after contacting with the predetermined target as compared to fluorescence of the plurality before contacting with the predetermined target, wherein the candidate deoxyribozyme attached to a microbead so recovered is identified as an aptamer for the predetermined target.

DETAILED DESCRIPTION OF THE INVENTION

Figures 1A, 1B, 1C, 1D:
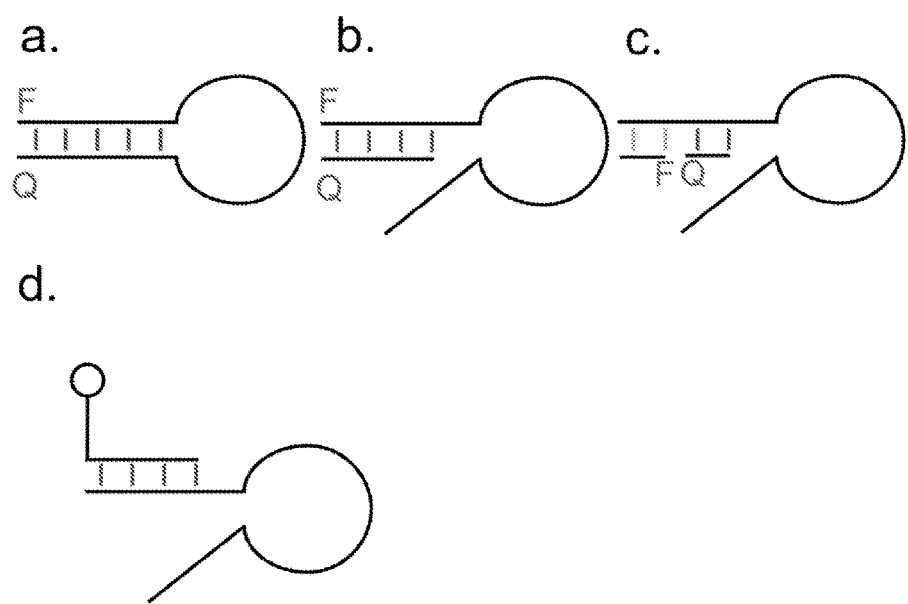
FIGS. 1(a)-1(d): Aptamers can be modified to generate fluorescent detection devices by (a) covalent attachment, (b) single-hybridization, or (c) dual-hybridization of quencher (Q) and fluorophore (F) dyes. Disruption of a duplex results in a strong fluorescent signal. (d) Classical structure-switching aptamer in vitro selection scheme.

This invention provides a method of identifying an aptamer for a predetermined target comprising:
contacting the predetermined target with a plurality of candidate oligonucleotide aptamers each attached to a microbead, wherein each candidate oligonucleotide aptamer (i) has hybridized thereto a second oligonucleotide having a fluorophore attached thereto, and (ii) also has hybridized thereto a third oligonucleotide having a quenching moiety attached thereto, wherein the third oligonucleotide having the quenching moiety is displaced from the candidate oligonucleotide aptamer if the candidate oligonucleotide aptamer binds to a target, and
recovering any microbeads that show an increase in fluorescence after contacting with the predetermined target as compared to fluorescence of the plurality before contacting with the predetermined target,
wherein the candidate oligonucleotide aptamer attached to a microbead so recovered is identified as an aptamer for the predetermined target.

In an embodiment, the plurality comprises a first plurality of candidate oligonucleotide aptamers each having the same sequence are attached to a single microbead, and at least a second plurality of candidate oligonucleotide aptamers each having the same sequence, but different to that of the first plurality, attached to a second single microbead. In an embodiment, the predetermined target is contacted with a plurality comprising multiple microbeads, each having a separate plurality of candidate oligonucleotide aptamers of the same first sequence attached to one microbead, a separate second plurality of candidate oligonucleotide aptamers of the same second sequence (different from the first sequence) attached to a second microbead and so on and so forth up to n pluralities. In an embodiment, n is between 2 and 500.

This invention also provides a method of identifying an aptamer for a predetermined target comprising:
contacting the predetermined target with a plurality of candidate oligonucleotide aptamers each attached to a microbead, wherein each candidate oligonucleotide aptamer (i) has hybridized thereto a second oligonucleotide having a first fluorophore of a FRET pair attached thereto, and (ii) also has hybridized thereto a third oligonucleotide having a second fluorophore of the FRET pair attached thereto, wherein the third oligonucleotide having the second fluorophore of the FRET pair is displaced from the candidate oligonucleotide aptamer if the candidate oligonucleotide aptamer binds to a target, and
recovering any microbeads that show a change in fluorescence after contacting with the predetermined target as compared to fluorescence of the plurality before contacting with the predetermined target,
wherein the candidate oligonucleotide aptamer attached to a microbead so recovered is identified as an aptamer for the predetermined target.

This invention also provides a method of identifying an aptamer for a predetermined target comprising:
contacting the predetermined target with a plurality of candidate oligonucleotide aptamers each attached to a microbead, wherein each candidate oligonucleotide aptamer (i) has attached thereto a fluorophore, and (ii) also has hybridized thereto another oligonucleotide having a quenching moiety attached thereto, wherein the oligonucleotide having the quenching moiety is displaced from the candidate oligonucleotide aptamer if the candidate oligonucleotide aptamer binds to a target, and
recovering any microbeads that show an increase in fluorescence after contacting with the predetermined target as compared to fluorescence of the plurality before contacting with the predetermined target,
wherein the candidate oligonucleotide aptamer attached to a microbead so recovered is identified as an aptamer for the predetermined target.

This invention also provides a method of identifying an aptamer for a predetermined target comprising:
contacting the predetermined target with a plurality of candidate oligonucleotide aptamers each attached to a microbead, wherein each candidate oligonucleotide aptamer (i) has hybridized thereto a first fluorophore of a FRET pair attached thereto, and (ii) also has hybridized thereto another oligonucleotide having a second fluorophore of the FRET pair attached thereto, wherein the oligonucleotide having the second fluorophore of the FRET pair is displaced from the candidate oligonucleotide aptamer if the candidate oligonucleotide aptamer binds to a target, and
recovering any microbeads that show a change in fluorescence after contacting with the predetermined target as compared to fluorescence of the plurality before contacting with the predetermined target,
wherein the candidate oligonucleotide aptamer attached to a microbead so recovered is identified as an aptamer for the predetermined target.

This invention also provides a method of identifying a deoxyribozyme for a predetermined target comprising:
contacting the predetermined target with a plurality of candidate deoxyribozymes each attached to a microbead, wherein each candidate deoxyribozyme (i) has attached thereto a fluorophore, and (ii) also has attached thereto a quenching moiety, wherein in the unbound state of the deoxyribozyme the fluorophore and quenching moiety are sufficiently far apart that the quenching moiety does not quench the fluorophore, and wherein when the deoxyribozyme binds to a target it folds such that the quenching moiety does quench the fluorophore, and recovering any microbeads that show an decrease in fluorescence after contacting with the predetermined target as compared to fluorescence of the plurality before contacting with the predetermined target, wherein the deoxyribozyme attached to a microbead so recovered is identified as an aptamer for the predetermined target.

This invention also provides a method of identifying an deoxyribozyme for a predetermined target comprising:

contacting the predetermined target with a plurality of candidate deoxyribozymes each attached to a microbead, wherein each candidate deoxyribozyme (i) has attached thereto a fluorophore, and (ii) also has attached thereto a quenching moiety, wherein in the unbound state of the candidate deoxyribozyme the fluorophore and quenching moiety are sufficiently close together that the quenching moiety quenches the fluorophore, and wherein when the candidate deoxyribozyme binds to a target it folds such that the quenching moiety does not quench the fluorophore, and recovering any microbeads that show an increase in fluorescence after contacting with the predetermined target as compared to fluorescence of the plurality before contacting with the predetermined target, wherein the candidate deoxyribozyme attached to a microbead so recovered is identified as an aptamer for the predetermined target.

In an embodiment of the methods, the method further comprises hybridizing the second oligonucleotide having the fluorophore attached thereto to the candidate beacon oligonucleotide aptamer having a fluorophore attached thereto prior to contacting the predetermined target.

In an embodiment of the methods, the method further comprises hybridizing the third oligonucleotide having the quenching moiety attached thereto to the candidate beacon oligonucleotide aptamer having a fluorophore attached thereto prior to contacting the predetermined target.

In an embodiment of the methods, the predetermined target is a protein, a peptide, a small organic molecule or a cell.

In an embodiment of the methods, recovering microbeads showing an increased fluorescence after contacting with the predetermined target is effected with fluorescence-assisted cell sorting (FACS).

In an embodiment of the methods, the candidate oligonucleotide aptamer is a candidate oligonucleotide beacon aptamer.

In an embodiment of the methods, the candidate oligonucleotide aptamer is single stranded prior to hybridization thereto of the second or third oligonucleotide.

In an embodiment of the methods, the quenching moiety comprises DABCYL, DABSYL, Eclipse, EDANS, Black hole quencher (BHQ)1, 2 and 3, QSY7, Iowa black, or black berry quencher (BBQ).

In an embodiment of the methods, the quenching moiety is attached to a 3' end of the third oligonucleotide.

In an embodiment of the methods, the fluorophore comprises FITC.

In an embodiment of the methods, the fluorophore is attached to a 5' end of the second oligonucleotide.

In an embodiment of the methods, the candidate oligonucleotide aptamer is attached to the microbead via a streptavidin-biotin linkage, an alkyne linkage, an amide linkage, a thioether linkage or a thioester linkage.

In an embodiment of the methods, the microbeads are paramagnetic or magnetic microbeads.

In an embodiment of the methods, the microbeads are of average diameter of 0.5 µm to 2 µm.

In an embodiment of the methods, the candidate oligonucleotide aptamer structurally comprises a two-way junction. In an embodiment of the methods, the candidate oligonucleotide aptamer structurally comprises a three-way junction. In an embodiment of the methods, the second and third oligonucleotides are 5' relative to the three-way junction. In an embodiment of the methods, the three-way junction comprises one or more variable sequences.

In an embodiment of the methods, the candidate oligonucleotide aptamer comprises DNA.

In an embodiment of the methods, the method further comprises amplifying the candidate oligonucleotide aptamer into multiple candidate oligonucleotide aptamers prior to attaching to microbeads.

In an embodiment of the methods, the amplifying is effected with emulsion PCR.

In an embodiment of the methods, the amplified candidate oligonucleotide aptamers are rendered single-stranded by applying NaOH thereto prior to hybridization with the second or third oligonucleotides.

In an embodiment of the methods, the method comprises only recovering the brightest 90%, or less, of microbeads having increased fluorescence.

In an embodiment of the methods, the method further comprises amplifying the oligonucleotide aptamers attached to the recovered microbeads. In an embodiment of the methods, the amplifying is effected with PCR.

In an embodiment of the methods, the method further comprises reiterating the method a second time, or a second time and third time, with the candidate oligonucleotide aptamer of each iteration being the candidate oligonucleotide aptamer identified as attached to the recovered microbeads of the previous iteration.

In an embodiment of the methods, the method further comprises cloning and sequencing the candidate oligonucleotide aptamer identified as attached to the recovered microbeads.

In an embodiment of the methods, no more than three iterations of the method are employed in identifying an aptamer for the predetermined target.

In an embodiment of the methods, the method further comprises identifying the microbeads having increased fluorescence by comparing fluorescence of the microbeads comprising the fluorescing candidate oligonucleotide aptamers to a control fluorescence amount, wherein an amount of fluorescence equal to or in excess of the control fluorescence amount identifies the microbeads as comprising fluorescing candidate oligonucleotide aptamers for the predetermined target.

In an embodiment of the methods, the control amount is determined from the fluorescence of a microbead comprising a fluorescing oligonucleotide without a quenching oligonucleotide attached thereto but bound to a target.

This invention also provides an aptamer comprising:

```
                                              (SEQ ID NO: 13)
ctcgggacgtaggattttcccttcggcacgaagtcgtcccgag (SEQ ID NO: 14)
ctcgggacgccggattttcccgagcacacgaagttgtcccgag
```

```
                                        (SEQ ID NO: 15)
ctcgggacagtggattttccagtccacacgaagttgtcccgag (SEQ ID NO: 16)
ctcgggacagtggattttcctatacacacgaagttgtcccgag (SEQ ID NO: 17)
ctcgggaccgtggattttccgagccacacgaagtggtcccgag
or (SEQ ID NO: 2)
ctcgggacgtggattttccacatacgaagttgtcccgag.
```

In an embodiment, the aptamers are selected from a library of N6 to N100. The apatamer lengths encompassed by the invention include the range limits as well as every integer inbetween, and every integer sub-range thereof.

In an embodiment, the aptamers herein are synthetic.

In an embodiment, the second oligonucleotide is not displaced on target binding. In an embodiment, the second and third oligonucleotides are sufficiently proximal such that the quenching moiety at least partially quenches the fluorophore. Quenching moieties and fluorophores are well known in the art. Non-limiting examples of fluorophores include FITC, cyanin dyes, Hydroxycoumarin, Aminocoumarin, Methoxycoumarin, Cascade Blue, Pacific Blue, Pacific Orange, Lucifer yellow, NBD, R-Phycoerythrin (PE), PE-Cy5 conjugates, PE-Cy7 conjugates, Red 613, PerCP, TruRed, FluorX, Fluorescein, BODIPY-FL, TRITC, X-Rhodamine, Lissamine Rhodamine B, Texas Red, Allophycocyanin (APC), APC-Cy7 conjugates, DAPI. The fluorophore and quenching moiety pairs (i.e. on the second and third oligonucleotides) of the invention are compatible pairs in that the quenching moiety quenches the particular fluorophore. Non-limiting examples of quenching moieties include DDQ-I, Dabcyl, Eclipse, Iowa Black, FQ BHQ-1, QSY-7, BHQ-2, DDQ-II, Iowa Black RQ, QSY-21, BHQ-3.

In an embodiment, the first and second fluorophore are a FRET pair, and binding displaces the third oligonucleotide such that the distance between the two fluorophores of the FRET pair alters, resulting in a change in fluorescence of the fluorophore of the FRET pair of the second oligonucleotide.

In an embodiment the target is a small organic molecule. In an embodiment, the small organic molecule is 2,000 daltons or less in mass.

In an embodiment of an aptamer of the invention, the aptamer comprises (a) (i) a 5' non-random region contiguous at its 3' end with (ii) a random region contiguous at its 3' end with (iii) a 3' non-random region; or (b) (i) a 5' non-random region contiguous at its 3' end with (ii) a random region contiguous at its 3' end with (iii) a second non-random region contiguous at its 3' end with (iv) a second random region contiguous at its 3' end with (v) a 3' non-random region.

In an embodiment of the methods, the aptamer is an oligodexoynucleotide. In an embodiment of the methods, the aptamer is an oligoribonucleotide. In an embodiment of the methods, the aptamer comprises both ribonucleotides and dexoynucleotides.

In an embodiment of the methods, the aptamer is a xeno nucleic acid (see, Pinhiero et al., Science 20 April 2012: Vol. 336 no. 6079 pp. 341-344, hereby incorporated by reference (19)).

In an embodiment, the aptamer is 20-175 nucleotides in length. In an embodiment, the aptamer is 25-150 nucleotides in length.

In an embodiment, the first oligonucleotide is 5-30 nucleotides in length. In an embodiment, the first oligonucleotide is one of 10, 11, 12, 13, 14, 15, 16, 17, 18, 19, 20, 21, 22, 23, 24, or 25 nucleotide residues in length. Each individual length is an embodiment of the invention. In an embodiment, the second oligonucleotide is 5-30 nucleotides in length. In an embodiment, the second oligonucleotide is one of 10, 11, 12, 13, 14, 15, 16, 17, 18, 19, 20, 21, 22, 23, 24, or 25 nucleotide residues in length. Each individual length is an embodiment of the invention.

In an embodiment, the random portion of the oligonucleotide(s) described herein is one of 10, 11, 12, 13, 14, 15, 16, 17, 18, 19, 20, 21, 22, 23, 24, or 25 nucleotide residues in length. Each individual length of the random portion is an embodiment of the invention. Total lengths of these oligonucleotides of 20 through 175 nucleotides are encompassed. Each individual integer in the series 20 through 175 as the total length is an embodiment of the invention.

In an embodiment of the method only the brightest 90% or less of microbeads are recovered. In an embodiment of the method only the brightest 80% or less of microbeads are recovered. In an embodiment of the method only the brightest 70% or less of microbeads are recovered. In an embodiment of the method only the brightest 60% or less of microbeads are recovered. In an embodiment of the method only the brightest 50% or less of microbeads are recovered. In an embodiment of the method only the brightest 40% or less of microbeads are recovered. In an embodiment of the method only the brightest 30% or less of microbeads are recovered. In an embodiment of the method only the brightest 25% or less of microbeads are recovered. In an embodiment of the method only the brightest 20% or less of microbeads are recovered. In an embodiment of the method only the brightest 15% or less of microbeads are recovered. In an embodiment of the method only the brightest 10% or less of microbeads are recovered. In an embodiment of the method only the brightest 5% or less of microbeads are recovered. In an embodiment of the method only the brightest 4, 3, 2 or 1% of microbeads are recovered. By the term "or less", no less than 0.5% is meant. In other words, a given percentage or less still requires recovering of some microbeads, and not none.

The phrase "and/or" as used herein, with option A and/or option B for example, encompasses the individual embodiments of (i) option A alone, (ii) option B alone, and (iii) option A plus option B.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group subjectly and all possible subgroups of the main group, but also the main group absent one or more of the group members. The present invention also envisages the explicit exclusion of one or more of any of the Markush group members in the claimed invention.

All combinations of the various elements described herein are within the scope of the invention unless otherwise indicated herein or otherwise clearly contradicted by context.

In the event that one or more of the literature and similar materials incorporated by reference herein differs from or contradicts this application, including but not limited to defined terms, term usage, described techniques, or the like, this application controls.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Figures 3A, 3B, 3C, 3D:
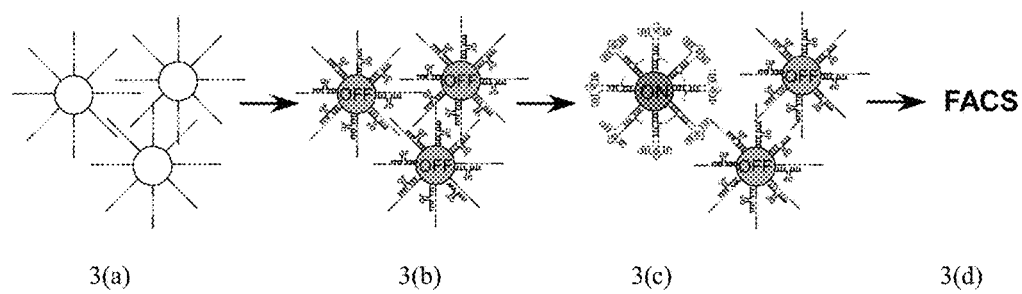
FIG. 3(a)-3(d): DNA libraries amplified by ePCR and rendered single stranded by treatment with NaOH (a) were hybridized to fluorophore (F) and quencher (Q) oligonucleotides generating libraries of particles in the 'OFF' state (b). Following incubation with target, particles which turn 'ON' in the presence of ligand (c) were recovered by FACS (d).

An in vitro selection scheme was devised that directly identifies structure-switching aptamer beacons that fluoresce in the presence of analyte by combining emulsion PCR (ePCR) and Fluorescence-Assisted Cell Sorting (FACS; FIG. 3). This approach enables the de novo selection of functional aptamer beacons without the need for further optimization and modification. Furthermore, because selection pressure in this approach is based on FACS gating, molecules with distinctly different functional properties can be identified.

Figure 2:
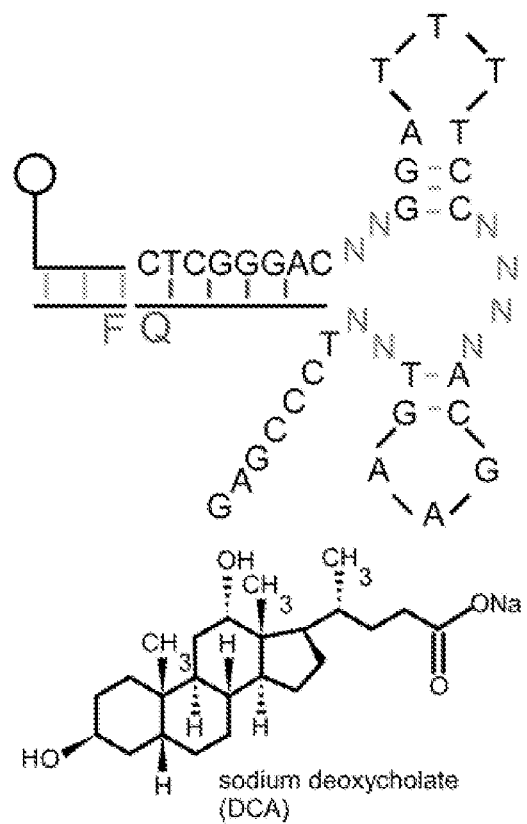
FIG. 2: Fluorescent structure-switching aptamer in vitro selection scheme for the "LN8" library used to identify three-piece aptamer beacon devices. Also shown are small molecules used in this selection.

In an embodiment, microbeads were loaded with copies of clonal, double-stranded DNA (dsDNA) by ePCR (14-17). These dsDNAs were rendered single stranded by brief treatment with NaOH and then annealed to adjacent 5' FITC- and 3' DABCYL-labeled oligonucleotides which lay 5' to a designed three-way junction that contains short variable regions (FIG. 2). Binding events that result in the release of the 3' DABCYL-labeled oligonucleotide cause the fluorescence of the bead to increase. The fluorescent beads can then be selectively sorted away from quenched beads by FACS.

It was initially sought to utilize this methodology to select for aptamers that bind DHEA-sulfate (DIS), a diagnostic of adrenal function, from a library based on a previously-explored aptamer beacon library (LN8). To begin each selection, streptavidin-coated microbeads were loaded with double-biotinylated-LN8 library (1:1), saturated with double-biotinylated primers and PCR-amplified in a water-oil emulsion (ePCR). Using this approach a population of beads of which ~40% contain ~40,000 copies of a single sequence (not shown) was routinely generated. Beads were recovered from the emulsion and subsequently treated with strong base to generate ssDNA. The ssDNA-covered beads were neutralized, and annealed to FITC—labeled oligonucleotides and DABCYL-labeled oligonucleotides before equilibration in binding buffer.

Figures 4A, 4B, 4C, 4D:
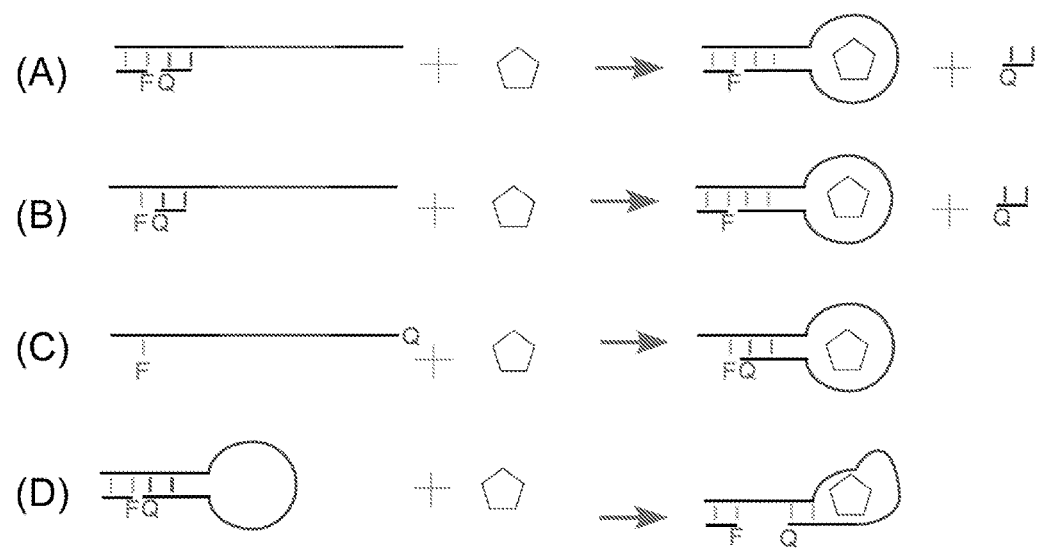
FIG. 4(a)-4(d): (a) Displacement where the quencher oligonucleotide bears a different fluorophore forming a FRET pair with the hybridized fluorescently labeled oligonucleotide; (b) Displacement where the quencher bearing oligonucleotide pairs with a fluorescent dye incorporated into the 5' primer attached to the bead. The fluorescent label is this part of the beacon molecule itself. This eliminates the need for hybridization of a complementary fluorescent oligonucleotide; (c) and (d) Structure switching without displacement. Incorporation of a fluorescent dye incorporated into the 5' primer attached to the bead and conjugation of a 2nd fluorophore or dye at the 3' end of the attached strand allows for the selection of sequences, with no hybridization. Library molecules can start open and fold in the presence of ligand (c) or folded and open (d), depending on library design.

Prior to each sort, a subset of beads bearing ssDNA was incubated with only the FITC-labeled oligonucleotide. This allowed identification of where the fully 'ON' positive events lay in the FACS histogram (FIG. 5a; ON). It is important to note that this control also allowed confirmation that the ePCR had been conducted successfully without mixing as indicated by the presence of a negative bead population corresponding to beads which did not get compartmentalized with library molecules (FIG. 5a; Blank). Following this analysis, the remaining pool was subsequently incubated with both FITC-labeled oligonucleotides and DABCYL-labeled oligonucleotides and library molecules in the 'OFF' state were sorted for fully-quenched beads (negative sort). This sorting gate was typically set to collect the ~75% darkest population and was preferred to purge the starting population of false positives—sequences that bound the FITC- but not the DABCYL-labeled oligonucleotides (FIG. 4b; 'OFF'). Beads in the 'OFF' state were collected, concentrated by centrifugation and then incubated in the presence of the target (DIS, 200 μM) for ~25 minutes. The beads were then sorted a second time and fluorescent events that occurred within the 'ON' gate defined by the FITC-oligonucleotide only analysis were collected. To impose stringency, only the brightest ~50% of the positive-control gated population were collected. DNAs from these sorted beads were recovered by PCR to generate an enriched library and used in subsequent rounds of selection (FIG. 5a-c; R1-R3).

Figure 5:
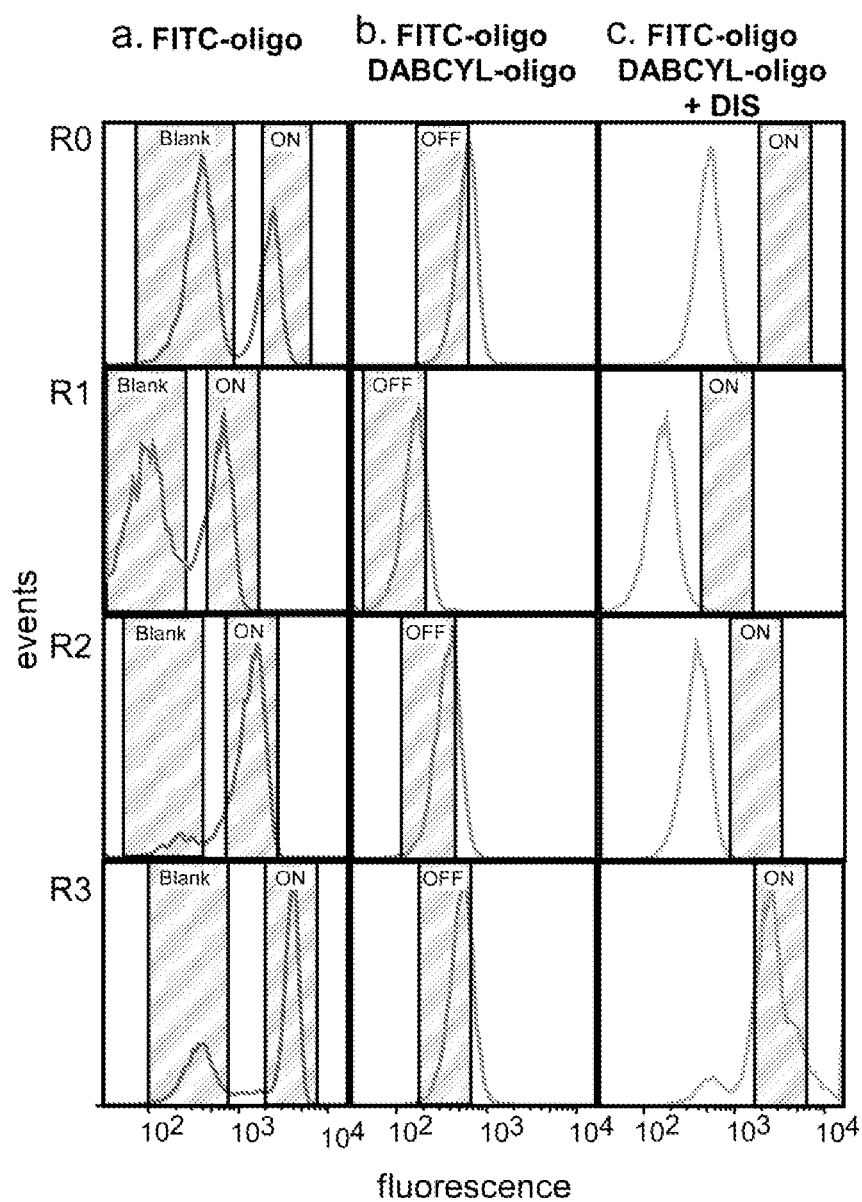
FIG. 5(a)-5(c): Progress of the LN8 DIS selection by flow cytometry. (a) Bead-bound LN8 library annealed to the FITC-oligonucleotide to determine the positive gates ("ON") and to confirm the presence of unlabeled beads indicating that the emulsion remained intact during PCR ("Blank"). (b) Following hybridization of the of the FITC-oligonucleotide and of the DABCYL-oligonucleotide, beads were quenched and sorted using the hashed gate ("OFF") to remove false positive events. (c) Positive selection was initiated by the addition of 200 μM DIS, and beads were sorted for positive events falling in the hashed gate ("ON"), which was set based on the data collected in (a). R0 data is derived from the initial LN8 library, R1 from the first enriched library, etc.

Following the third round of selection, the LN8 population displayed marked enrichment for functional binders as evidenced by a substantial fraction of positively fluorescent events (FIG. 5d; R3). To identify these sequences, DNA recovered from the last round of selection was cloned and sequenced. 85 out of 90 sequences show high homology to the previously-selected "diss.1" aptamer 13 (Table 1). This newly identified aptamer differs from the diss.1 aptamer in one position, where a G is replaced with an A: hence the designation of this aptamer as "diss.1A". In the previously hypothesized structure for diss.1,13 this G to A transition might replace a G-T wobble with an A-T WC pairing.

To identify any effects this transition may have on aptamer activity, both sequences were assayed by a FACS-based activity assay. Beads loaded with ssDNA were annealed to 5' FITC- and 3' DABCYL-labeled oligonucleotides in binding buffer. The beads were then incubated in the presence of increasing concentrations of DIS or a structurally related compound, deoxycholate salt (DCA), for forty minutes and then analyzed by FACS (FIG. 6). In contrast to aptamer beacons isolated from previous selection schemes (9-13) these assays were simplified, as these aptamer beacons are already capable of fluorescence based detection and can be utilized to detect analyte without any additional modification.

Figures 6A, 6B:
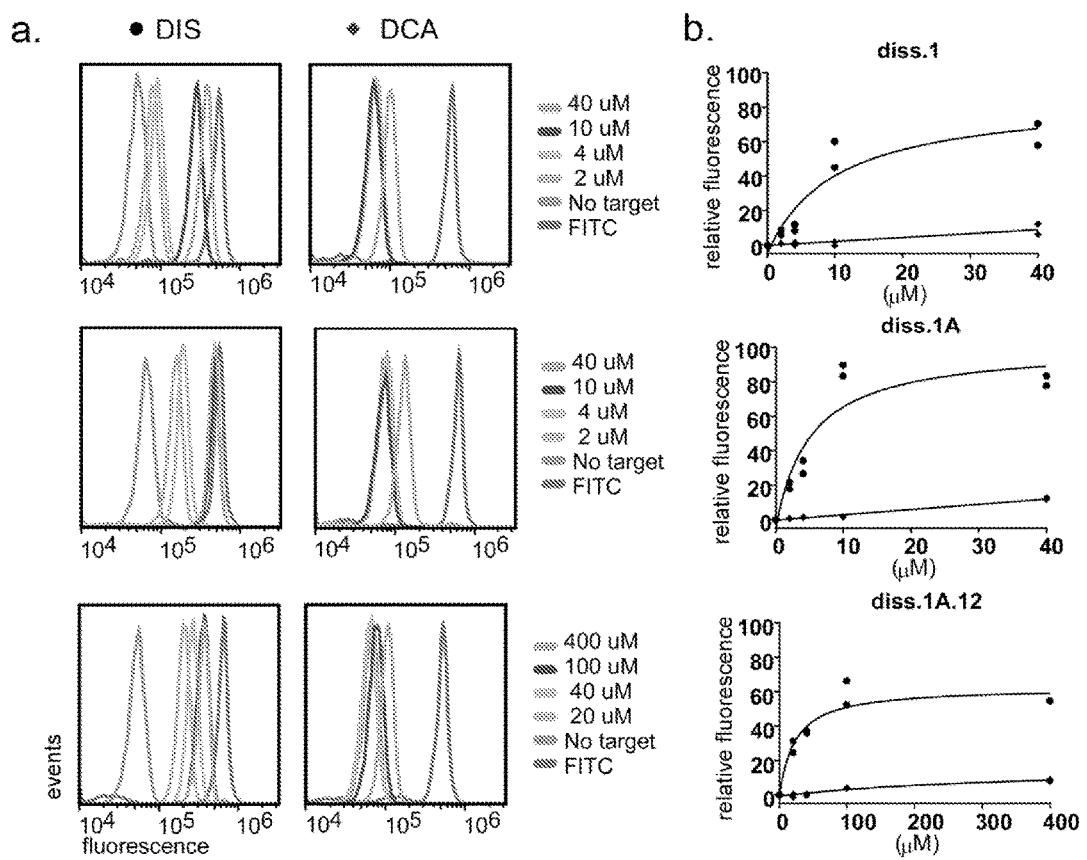
FIG. 6(a)-6(b): Binding activity of the diss.1 family of DIS aptamers. (a) Representative flow cytometry histograms of aptamers incubated in the presence of increasing concentrations of DIS (left) or DCA (right), note scale. All experiments contained a sample reaction performed in the absence of target (No target) or bearing only the FITC-labeled oligonucleotide (FITC) representing the signal expected from a construct which had turned fully "ON". (b) Binding curves determined by plotting the mode of relative fluorescence of two independent experiments. Apparent binding constants for diss.1, diss.1.A and diss.1.A.12 are 10.3, 5.1, and 22.6 µM, respectively.
Figure 7:
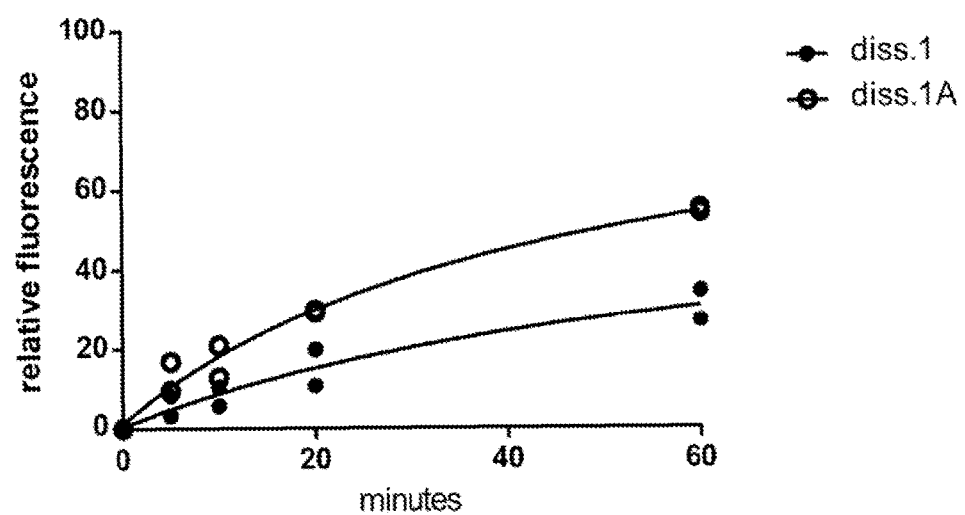
FIG. 7: Time-course binding activity of diss.1 and diss.1A for DIS (15 µM). Binding curves were determined by plotting the mode of relative fluorescence of two independent experiments.

Previously, in a plate reader-based fluorescence assay, a re-engineered variant of the diss.1 aptamer, optimized for fluores-cence signaling, was shown to fluoresce in the presence of lower concentrations of DIS (~1 μM) and to have no fluorescence in the presence of similar concentrations of DCA.13 Accordingly, the flow-cytometry based assay is in qualitative agreement with both of these findings (FIG. 6). A comparison of diss.1 and diss.1A binding activity profiles suggests the difference in their sequences has little consequence on specificity, though the relative fluorescence of the diss.1A aptamer is greater at all tested concentrations of DIS (FIG. 6b). Further, the fluorescence of diss.1A-loaded beads increases more readily over time (FIG. 7). The increased sensitivity of the diss.1A aptamer may have allowed it to outcompete the diss.1 aptamer, which was not identified in sequences recovered from the final round of this selection (Table 1).

Figures 8A, 8B, 8C:
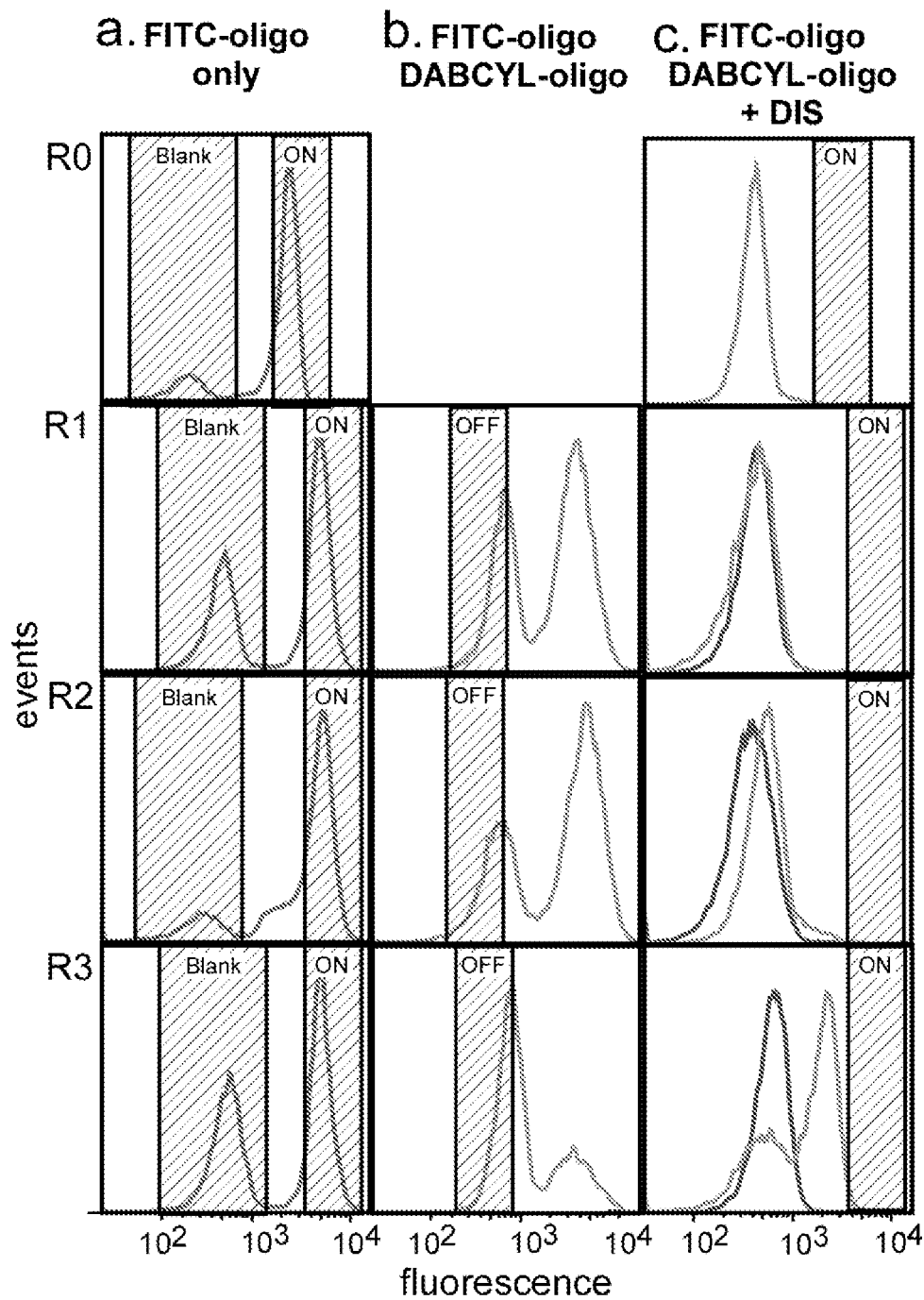
FIG. 8(a)-8(c): Progress of the LN12 DIS selection by flow cytometry. Bead-bound LN12 library annealed to (a) the FITC-oligonucleotide to determine the positive gates ("ON"), or (b) both the FITC- and DABCYL-oligonucleotides to sort quenched beads ("OFF"). (c) DIS (200 µM) was added to quenched, sorted beads (grey) and re-sorted for positive events ("ON") (orange). The negative sort was omitted in the first round. R0 data is derived from the initial LN12 library, R1 from the first enriched library, etc.
Figures 9A, 9B:
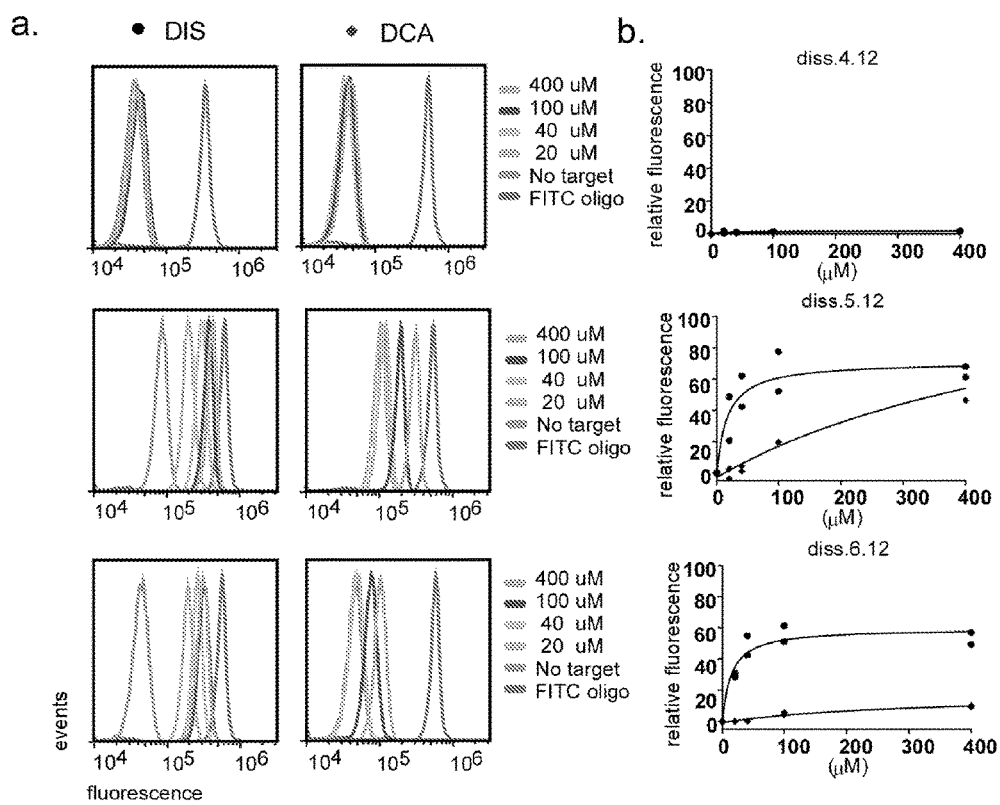
FIG. 9(a)-9(b): Binding activity of sequences isolated from the LN12 selection. (a) Representative flow cytometry histograms of binding activity to DIS (left) or DCA (right) for indicated sequences. (b) Binding curves were determined by plotting the mode of relative fluorescence of two independent experiments.

Next, it was reasoned that a more complex library might contain aptamers with more sensitive, improved device responses. Thus, a second selection was carried out for DIS-responsive aptamer beacons in which four additional variable positions were introduced into the three-way junction structure creating a library with a complexity of $~10^7$ variants, LN12 (FIG. 7, Table 1). This selection was carried out in a similar manner as the LN8 selection, except that the negative sort was omitted in the first round (FIG. 8b). This was necessary to maximize the diversity of recovered functional sequences, since a large fraction of beads (>50%) are lost between negative and positive sorts due to stringent FACS-logic gates and physical manipulation. This is a valid concern when working with libraries that contain twelve or more random base positions, which are characterized by a complexity ($~10^7$) that is near the number of beads used here ($~10^8$). As a consequence of the reduced stringency in the initial round, a "false positive" population was observed in every round, though it was largely selected against by the final round (FIG. 8b-d). As in the LN8 selection, a small positive fraction of events was observed with ligand-induced fluorescence from the third round of enriched DNA library. 93 sequences from the final, fourth, round recovered DNA library were cloned and sequenced. Interestingly, the three most frequently occurring sequences displayed a high level of similarity to sequences identified in the previous DIS-responsive aptamer beacon selection 13 (Table 1). The most frequent sequence, diss.1A.12 (28 copies), bears a high resemblance to the diss.1A aptamer, but the presence of additional bases demonstrates that it is clearly derived from the LN12 library. The second and third most frequent sequences, diss.3.12 and diss.4.12, are similar to sequences previously reported by Yang and colleagues13 (clone #47 and clone #42, respectively). Two novel sequences, diss.5.12 and diss.6.12, were also identified. Although, these sequences were isolated from a more highly diverse library, these aptamers required higher concentrations of analyte for detectable fluorescence activity. Further, diss.5.12, but not diss.6.12, binds DCA nearly as readily as DIS (FIG. 9; Table 1). These results indicate that the additional bases introduced into this library allow for greater flexibility in the designed binding pocket. Thus, the LN8 library may be restricted in its ability to form hydrophobic pockets capable of accommodating different ligands whereas the LN12 library, which is significantly more diverse, is not. Additionally, it is interesting to note that the responsiveness of selected variants from the LN12 library was ~10-fold worse than those of the LN8 library suggesting that the additional bases may perturb the responsiveness of library, a consideration for future structured library designs.

The ability to use FACS to screen libraries of oligonucleotides for the ability to switch structure and signal the presence of analytes presents a number of significant advantages over previous selection technologies. In particular, unlike almost all other approaches, this selection approach allows for the ability to directly identify signaling molecules. Thus, molecules selected can be readily synthesized and used to generate detection agents with little or no additional engineering or optimization. Furthermore, because the selective pressure is imposed by FACS gating, the selection can potentially be tuned to identify molecules with particular properties (e.g., maxima response, activation kinetics). Although this approach has been used here to search small libraries ($\sim 10^5$-$10^7$), as many as $10^8$ events can be screened per hour on most high throughput sorters (~30,000 events/sec) allowing for selection using larger libraries. This number could be further increased by including multiple sequences per beads during the early rounds of selection and then decreasing the number of variants per bead for the later round as described for other compartmentalization-based selection schemes (18). For example, initial rounds of selection with 1000 sequences per bead could increase the library complexity to $\sim 10^{11}$, although such a selection would require significant increases in the sensitivity of detection. Finally, the approach could be combined with other more traditional selection schemes that allow for pre-selection of structural-switching aptamers from much larger libraries ($\sim 10^{14}$-$^{16}$) or even extended to the selection of other oligonucleotide based signaling molecules such as allosteric deoxyribozymes.

TABLE 1

Sequences retrieved from the LN8 and LN12 DNA aptamer beacon libraries, highlighting the conserved stem (italicized), variable (bold) and selected (underlined) positions. Empty spaces are inserted for alignment of sequence similarity. Sequences retrieved in a previous selection (13) marked (*). SEQ ID NOS 1-17, top to bottom, respectively.

| Name | Sequence 5'-3' | Activity | Count |
|---|---|---|---|
| LN8 library | *CTCGGGAC*__NN__*GGATTTTCC*__NNNN__*ACGAAGT*__NN__*TCCCGAG* | | |
| diss.1A | CTCGGGAC__GT__GGATTTTCC__ACAT__ACGAAGT__TG__TCCCGAG | +++ | 85/90 |
| diss.1* | CTCGGGAC__GT__GGATTTTCC__GCAT__ACGAAGT__TG__TCCCGAG | +++ | |
| diss.2 | CTCGGGAC__AT__GGATTTTCC__ATAA__ACGAAGT__GG__TCCCGAG | ND | 4/90 |
| Dis6th-#43 | GAC__AT__GGATTTTCC__ATAA__ACGAAGT__GGG__TC | | |
| LN12 library | *CTCGGGAC*__NNN__*GGATTTTCC*__NNNNNNN__*ACGAAGT*__NN__*TCCCGAG* | | |
| diss.1A.12 | CTCGGGAC__GTT__GGATTTTCC__CAAACAT__ACGAAGT__TG__TCCCGAG | + | 28/93 |
| diss.1* | CTCGGGAC__GT__ GGATTTTCC __GCAT__ACGAAGT__TG__TCCCGAG | | |
| diss.3.12 | CTCGGGAC__GTT__GGATTTTCC__TATACTA__ACGAAGT__GG__TCCCGAG | ND | 16/93 |
| Dis6th-#47* | GAC__GT__ GGATTTTCC __ACTA__ACGAAGT__GGG__TC | | |
| diss.4.12 | CTCGGGAC__TCA__GGATTTTCC__ATCCGGT__ACGAAGT__AG__TCCCGAG | - | 10/93 |
| Dis6th-#42* | GAC __ACG__GATTTTCC __TCCG__ ACGAAGT__GA__GTC | | |
| diss.5.12 | CTCGGGAC__GTA__GGATTTTCC__CTTCGGC__ACGAAGT__CG__TCCCGAG | + | 8/93 |
| diss.6.12 | CTCGGGAC__GCC__GGATTTTCC__CGAGCAC__ACGAAGT__TG__TCCCGAG | + | 5/93 |

TABLE 1-continued

Sequences retrieved from the LN8 and LN12 DNA aptamer beacon libraries, highlighting the conserved stem (italicized), variable (bold) and selected (underlined) positions. Empty spaces are inserted for alignment of sequence similarity. Sequences retrieved in a previous selection (13) marked (*). SEQ ID NOS 1-17, top to bottom, respectively.

| Name | Sequence 5'-3' | Activity | Count |
|---|---|---|---|
| diss.6.12-related | CTCGGGACAGTGGATTTTCCAGTCCACACGAAGTTGTCCCGAG | ND | 5/93 |
| | CTCGGGACAGTGGATTTTCCTATACACACGAAGTTGTCCCGAG | ND | 5/93 |
| | CTCGGGACCGTGGATTTTCCGAGCCACACGAAGTGGTCCCGAG | ND | 1/93 |

Figures 10A, 10B:
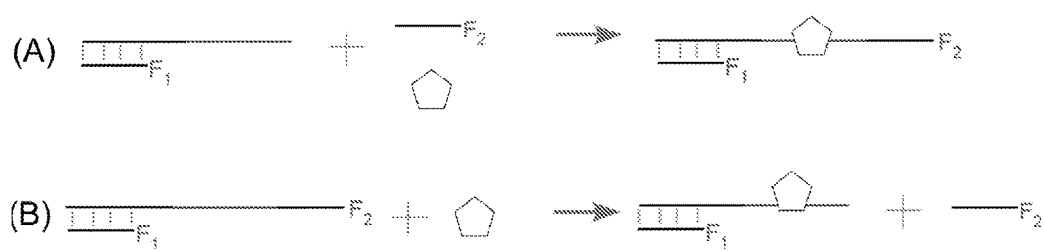
FIG. 10(a)-10(b). Deoxyribozyme libraries can be attached to the beads in the same fashion. In the presence of ligand they will either cleave themselves (b), releasing an appended fluorophore or (a) attach a fluorophore to themselves. The pentagon represents a ligand.

Deoxyribozyme libraries can similarly be attached to the beads in the same fashion. In the presence of ligand they will either cleave themselves (FIG. 10b), releasing an appended fluorophore or (FIG. 10a) attach a fluorophore to themselves. The pentagon represents a ligand.

Methods and Materials

Nucleic Acid Sequences:

```
Double-biotinylated primer:
B-B-CTGGTCATGGCGGGCATTTAATTCAATT

5' FITC-labeled oligonucleotide:
                                   (SEQ ID NO: 18)
FAM-CCTCAATACCACCACGTATTCATGCGAGATGGCC 3' DABCYL-labeled oligonucleotide:
                                   (SEQ ID NO: 19)
GTCCCGAGAGCAG-Dab Forward primer:
                                   (SEQ ID NO: 20)
CTGGTCATGGCGGGCATTTAATTCAATTACGTGGTCATCGTCCTGGTGG
CCATCTCGC Reverse primer:
                                   (SEQ ID NO: 21)
AGTCGTACGTTAGGAGGACT LN8 library:
                                   (SEQ ID NO: 22)
CTGGTCATGGCGGGCATTTAATTCAATTACGTGGTCATCGTCCTGGTGG
CCATCTCGCATGAATACGTGGTGGTATTGAGGCTGCTCTCGGGACNNGG
ATTTTCCNNNNNACGAAGTNNTCCCGAGTCCTCCTAACGTACGACT LN12 library:
                                   (SEQ ID NO: 23)
CTGGTCATGGCGGGCATTTAATTCAATTACGTGGTCATCGTCCTGGTGG
CCATCTCGCATGAATACGTGGTGGTATTGAGGCTGCTCTCGGGACNNNG
GATTTTCCNNNNNNNACGAAGTNNTCCCGAGTCCTCCTAACGTACGACT
```

Oligonucleotides and libraries were synthesized by IDT (Coralville, Iowa) with the exception of the double biotinylated primer which was synthesized in house by standard solid phase DNA synthesis using an Expedite 8909 DNA synthesizer. The double biotin was put on during synthesis using two successive couplings of a Biotin-TEG-phosphoramidite. The oligonucleotide was synthesized DMT-ON and, following standard deprotection, purified by reverse phase HPLC using a Waters Xbridge C18 column heated at 60° C., using 0.1M triethylammonium acetate pH 7.5 and a linear gradient of acetonitrile. Following purification, the trityl group was removed by brief (20 min) treatment with 80% acetic acid, and the trityl achohol was removed by extraction with ethyl acetate. All synthesis reagents were purchased from Glen Research (Sterling, Va.).

Emulsion PCR: ~2.1×10$^8$ MyOne streptavidin-coated magnetic beads (Life Technologies, 1 µm, 30 µl) were washed and resuspended in 50 µl of B+W buffer (10 mM Tris pH 8.5, 2 M NaCl, 1 mM EDTA) by collecting the MyOne Streptavidin-coated beads over a neodymium magnet (2 cm$^3$). 30 pg of LN8 or LN12 double-biotinylated DNA library dissolved in 50 µl of dH$_2$O were mixed by pipetting, vortexed briefly and shaken for 15 minutes. Beads were then saturated by adding 30 µl of double-biotinylated primer (10 µM) to the mix for an additional 15 minutes on a shaker. The beads were then washed by five 200 µl washes of 1× PCR buffer. 200 µl of PCR mix was added to the beads and mixed by pipetting.

PCR Mix:
Forward primer, 50 nM
Reverse primer, 8 µM
dNTPs, 200 µM each
BSA, 0.5 mg/mL (prepared at 10 mg/mL, filtered by 0.46 micron)
1×PCR buffer
16 µl Taq (2 U/µl)
Oil:
584 µl Tegosoft WEC
160 µl Sigma light mineral oil
56 µl WE09

The oil was mixed fresh daily in a cryosoft tube, briefly vortexed and allowed to sit at room temperature for at least 30 minutes.

The water-in-oil emulsion was prepared by adding PCR mix to the oil in a dropwise fashion over the course of 1 minute over a bed of ice while mixing with a Spinplus cross-stirbar (⅜") at 1250 rpm. The entire water-in-oil emulsion was mixed for an additional three minutes. The emulsified PCR reactions were aliquoted into five standard 250 µl PCR tubes and thermocycled.

PCR Cycle Parameters:
1. 90° C. 45 s
2. 94° C. 15 s
3. 55° C. 38 s
4. 72° C. 75 s
5. Go to 2. 36 times
6. 72° C. 5 m It was found that >36 cycles resulted in visible compartmental breakage.

Recovery of beads from emulsion: 750 µl butanol was added to a similar volume of the emulsion and mixed by pipetting 500 µl PB (5M guanidine HCL, 30% isopropanol with 20 mM Tris pH6.8) was added to the broken emulsion and briefly vortexed. Beads were pelleted (6,000×g for 5 minutes) and washed in PB once (500µ).

Preparation of the ssDNA functionalized particles: Beads were collected by magnet, and 30 µl of NaOH (0.1 M) was added. Beads were sonicated for a quick pulse (<1 sec) and shaken for 5 minutes, twice. Beads were neutralized with TBST, then washed several times with PBS. Saturating levels of FITC- and DABCYL-oligonucleotides were annealed to the bead-immobilized DNA in PBS at room temperature for at least 15 minutes. Excess oligonucleotides were removed by three PBS washes (100 µl each). Beads were then washed in Selection Buffer (20 mM Tris pH 7.5, 1 M NaCl, 10 mM MgCl2) three times (100 µl each).

Quantitation of ePCR amplification on the bead: To determine the number of DNA molecules on each bead, beads that were amplified by ePCR were compared to beads loaded with known amounts of DNA and analyzed by FACS. It was found that a shorter (42 instead of 84 base) linker between the bead and FITC moiety resulted in a weak fluorescence signal (not shown). This may be due to absorption of light by the dark, iron particle.

FACS sorting parameters: Beads were sorted by a FACS Aria3 using a 70 µM nozzle at ~10,000 events/sec. Prior to sorting, drop delay was determined by standard Accudrop protocols, and the filter was removed for detection of the small beads. All sorts were carried out in the "single-cell" mode, which discards droplets that are positive but that contain negative events. For negative sorts, the "bottom" (left-most) 75% of the quenched population was collected. For positive sorts, the "top" (right-most) 50% of the unquenched population was collected. For negative sorts collected in the absence of target (to purge false positives), at least ten million beads were collected for the subsequent positive sort. This guaranteed full coverage of the initial starting complexity of the library (~$10^5$ for the LN8 library, and ~$10^6$ of the second round of the LN12 library), taking the large fraction of beads lost during collection into account. For positive sorts, beads were collected until the entire sample was exhausted (typically between 500 and several thousand beads). DIS was dissolved in methanol and did not exceed 0.2% of the final selection assay volume. Negative sorts were run in the presence of 0.2% methanol.

Bead collection and re-annealing between negative and positive sorts: For concentrating negatively-sorted beads from large volumes, 10% TBST was added to the flow-through, and eluant was centrifuged in 15 mL conicals at 12,000×g for 15 min. The conicals were rotated in the bucket to prevent aggregation on the walls of the tubes and centrifuged at the same speed for an additional 15 minutes.

For concentrating negatively sorted beads from smaller volumes, 10% TBST was added to the flow-through and centrifuged in 1.5 mL microcentrifuge tubes at 15,000×g for 5 min.

Collected beads were washed in PBS and re-annealed to excess 5' FITC-labeled and 3' DABCYL-labeled oligonucleotides, washed in PBS, and then washed and equilibrated in binding buffer before the addition of DIS (200 µM) for ~25 min prior to positive sorting.

Recovery of bead-bound DNA by PCR: TBST (10% final) and ~40,000 blank, carrier beads were added to the solution of post-postively-sorted beads (in FACS buffer) and centrifuged for 10 minutes at 16,000×g. Control PCR reactions containing known amounts of beads bound to ~40,000 copies of DNA library each provided a valuable estimate for how many cycles were required. Thus, tracking the amount of positive beads sorted allowed us to estimate the required amount of cycles with high accuracy. PCR mix was standard except for the addition of 0.5 mg/mL BSA.

Recovery PCR Parameters:
1. 90° C. 45 s
2. 94° C. 15 s
3. 55° C. 38 s
4. 72° C. 55 s
5. Go to 2. X times
6. 72° C. 25 s
X was typically ~20 cycles for 700 beads, ~18 cycles for 7,000 beads.

FACS-based binding activity assays: 300 ng of double-biotinylated DNA were incubated with 1 µl of MyOne streptavidin-coated magnetic beads (1 µm) in B+W buffer on a shaker for one hour at room temperature (60 µl final volume). Beads were washed (100 µl) and resuspended in 0.1 M NaOH (30 µl), briefly sonicated (<1 sec) and incubated on a shaker for 5 minutes. This step was repeated once to fully break-up any aggregates and to thoroughly release unbound DNA. Beads were washed and neutralized in PBS (pH 7.0, 60 µl final volume) and annealed to saturating amounts of 5' FITC-labeled oligonucleotide (0.3 µl of 100 µM stock) by heating at 50° C. for 15 sec and cooling to room temperature. 3' DABCYL-labeled oligonucleotide (0.9 µl of 100 µM stock) was annealed at room temperature, and free oligonucleotides were washed three times with selection buffer (100 µl each). Aliquots of beads were then incubated in the presence or absence of DIS or DCA in Selection Buffer for 40 minutes (or a time course) and analyzed by FACS.

REFERENCES (1) Wang, K.; Tang, Z.; Yang, C. J.; Kim, Y.; Fang, X.; Li, W.; Wu, Y.; Medley, C. D.; Cao, Z.; Li, J.; Colon, P.; Lin, H.; Tan, W. *Angew Chem Int Ed Engl* 2009, 48, 856.

(2) Liu, J.; Cao, Z.; Lu, Y. *Chem Rev* 2009, 109, 1948.

(3) Nutiu, R.; Li, Y. *Methods* 2005, 37, 16.

(4) Fang, X.; Sen, A.; Vicens, M.; Tan, W. *Chembiochem* 2003, 4, 829.

(5) Hamaguchi, N.; Ellington, A.; Stanton, M. *Anal Biochem* 2001, 294, 126.

(6) Stojanovic, M. N.; de Prada, P.; Landry, D. W. *J Am Chem Soc* 2001, 123, 4928.

(7) Yamamoto, R.; Baba, T.; Kumar, P. K. *Genes Cells* 2000, 5, 389.

(8) Nutiu, R.; Li, Y. *J Am Chem Soc* 2003, 125, 4771.

(9) Morse, D. P. *Biochem Biophys Res Commun* 2007, 359, 94.

(10) Nutiu, R.; Li, Y. *Angew Chem Int Ed Engl* 2005, 44, 1061.

(11) Oh, S. S.; Plakos, K.; Lou, X.; Xiao, Y.; Soh, H. T. *Proc Natl Acad Sci USA*, 107, 14053.

(12) Rajendran, M.; Ellington, A. D. *Anal Bioanal Chem* 2008, 390, 1067.

(13) Yang, K. A.; Pei, R.; Stefanovic, D.; Stojanovic, M. N. *J Am Chem Soc* 2013, 134, 1642.

(14) Kojima, T.; Takei, Y.; Ohtsuka, M.; Kawarasaki, Y.; Yamane, T.; Nakano, H. *Nucleic Acids Res* 2005, 33, e150.

(15) Diehl, F.; Li, M.; He, Y.; Kinzler, K. W.; Vogelstein, B.; Dressman, D. *Nat Methods* 2006, 3, 551.

(16) Dressman, D.; Yan, H.; Traverso, G.; Kinzler, K. W.; Vogelstein, B. *Proc Natl Acad Sci USA* 2003, 100, 8817.

(17) Schutze, T.; Rubelt, F.; Repkow, J.; Greiner, N.; Erdmann, V. A.; Lehrach, H.; Konthur, Z.; Glokler, *J. Anal Biochem,* 410, 155.

(18) Zheng, Y.; Roberts, R. J. *Nucleic Acids Res* 2007, 35, e83.

(19) Science 20 Apr. 2012: Vol. 336 no. 6079 pp. 341-344.

What is claimed:

1. A method of identifying a structure switching aptamer for a predetermined target without need for further modification, comprising:
  contacting the predetermined target with a plurality of candidate oligonucleotide aptamers each attached to a microbead, wherein each candidate oligonucleotide aptamer structurally comprises a three-way junction and (i) has hybridized thereto a second oligonucleotide having a fluorophore attached thereto, and (ii) also has hybridized thereto a third oligonucleotide having a quenching moiety attached thereto, wherein the third oligonucleotide having the quenching moiety is displaced from the candidate oligonucleotide aptamer if the candidate oligonucleotide aptamer binds to a target, and
  recovering, by fluorescence-assisted cell sorting, any microbeads that show an increase in fluorescence after contacting with the predetermined target as compared to fluorescence of the plurality before contacting with the predetermined target, and
  cloning and sequencing oligonucleotides from the recovered microbeads,
  wherein the candidate oligonucleotide aptamer so cloned and sequenced is identified as a structure switching aptamer without need for further modification for the predetermined target.

2. The method of claim 1, further comprising hybridizing the second oligonucleotide having the fluorophore attached thereto to the candidate beacon oligonucleotide aptamer having a fluorophore attached thereto, for one or more candidate oligonucleotide aptamers of the plurality, prior to contacting the predetermined target.

3. The method of claim 1, further comprising hybridizing the third oligonucleotide having the quenching moiety attached thereto to the candidate beacon oligonucleotide aptamer having a fluorophore attached thereto, for one or more candidate oligonucleotide aptamers of the plurality, prior to contacting the predetermined target.

4. The method of claim 1, wherein the predetermined target is a protein, a peptide, a small organic molecule or a cell.

5. The method of claim 1, wherein the plurality of candidate oligonucleotide aptamers comprises candidate oligonucleotide beacon aptamers.

6. The method of claim 1, wherein the candidate oligonucleotide aptamers of the plurality are single stranded prior to hybridization thereto of the second or third oligonucleotide.

7. The method of claim 1, wherein the quenching moiety comprises DABCYL, DABSYL, Eclipse, EDANS, Black hole quencher (BHQ) 1, 2 and 3, QSY7, Iowa black, or black berry quencher (BBQ).

8. The method of claim 1, wherein the quenching moiety is attached to a 3' end of the third oligonucleotide.

9. The method of claim 1, wherein the fluorophore comprises FITC.

10. The method of claim 1, wherein the fluorophore is attached to a 5' end of the second oligonucleotide.

11. The method of claim 1, wherein the candidate oligonucleotide aptamer is attached to the microbead via a streptavidin-biotin linkage, an alkyne linkage, an amide linkage, a thioether linkage or a thioester linkage.

12. The method of claim 1, wherein the microbeads are paramagnetic or magnetic microbeads.

13. The method of claim 1, wherein the microbeads are of average diameter of 0.5 µm to 2 µm.

14. The method of claim 1, wherein the second and third oligonucleotides are 5' relative to the three-way junction.

15. The method of claim 1, wherein the three-way junction comprises one or more variable sequences.

* * * * *